US008313777B2

(12) United States Patent
Maitra et al.

(10) Patent No.: US 8,313,777 B2
(45) Date of Patent: Nov. 20, 2012

(54) WATER-DISPERSIBLE ORAL, PARENTERAL, AND TOPICAL FORMULATIONS FOR POORLY WATER SOLUBLE DRUGS USING SMART POLYMERIC NANOPARTICLES

(75) Inventors: Anirban Maitra, Baltimore, MD (US); Georg Feldmann, Bonn, DE (US); Savita Bisht, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1446 days.

(21) Appl. No.: 11/867,918

(22) Filed: Oct. 5, 2007

(65) Prior Publication Data

US 2008/0107749 A1 May 8, 2008

Related U.S. Application Data

(60) Provisional application No. 60/849,684, filed on Oct. 5, 2006, provisional application No. 60/866,516, filed on Nov. 20, 2006, provisional application No. 60/956,760, filed on Aug. 20, 2007.

(51) Int. Cl.
*A61K 9/58* (2006.01)

(52) U.S. Cl. ........................................ 424/501; 424/400

(58) Field of Classification Search ........................ None
See application file for complete search history.

(56) References Cited

U.S. PATENT DOCUMENTS

| | | | | |
|---|---|---|---|---|
| 5,648,506 A * | 7/1997 | Desai et al. | ................... | 549/510 |
| 6,322,817 B1 * | 11/2001 | Maitra et al. | .................. | 424/489 |
| 6,579,519 B2 | 6/2003 | Maitra et al. | | |

FOREIGN PATENT DOCUMENTS

| | | | |
|---|---|---|---|
| IN | 200300613 | * | 6/2005 |
| WO | WO 01/21174 | | 3/2001 |

OTHER PUBLICATIONS

Gupta, A.K., et al., "Ketorolac Entrapped in Polymeric Micelles: Preparation Characterisation and Ocular Anti-Inflammatory Studies", Int'l J. of Pharm. 209 (2000) pp. 1-14—XP-002636633.

Bisht, S., et al., "Polymeric Nanoparticle-Encapsulated Curcumin ("nanocurcumin"): A Novel Strategy for Human Cancer Therapy", J. of Nanobiotechnology, 5:3, (2007), pp. 1-18.

* cited by examiner

*Primary Examiner* — Michael G Hartley
*Assistant Examiner* — Robert Cabral
(74) *Attorney, Agent, or Firm* — Whitham Curtis Christofferson & Cook, PC

(57) ABSTRACT

Polymeric nanoparticles with a hydrophobic core and a hydrophilic shell are formed from: 1) N-isopropyl acrylamide (NIPAAM), at a molar ratio of about 50% to about 90%, and preferably 60% for specific delivery routes such as oral or parenteral; either water-soluble vinyl derivatives like vinylpyrolidone (VP) or vinyl acetate (VA), or water insoluble vinyl derivatives like methyl methacrylate (MMA) or styrene (ST), at a molar ratio of about 10% to about 30%; and acrylic acid (AA), at a molar ratio of about 10% to about 30%. The formed nanoparticles may be optionally surface functionalized using reactive groups present in AA, including PEGylation, or conjugation of moieties such as chemotherapeutics, contrasting agents, antibodies, radionucleides, ligands, and sugars, for diagnostic, therapeutic, and imaging purposes. The polymeric nanoparticles are preferably dispersed in aqueous solutions. The polymeric nanoparticles incorporate one or more types of medicines or bioactive agents in the hydrophobic core; on occasion, the medicine or bioactive agent may be conjugated to the nanoparticle surface via reactive functional groups. The polymeric nanoparticles are capable of delivering the said medicines or bioactive agents through oral, parenteral, or topical routes. The polymeric nanoparticles allow poorly water soluble medicines or bioactive agents, or those with poor oral bioavailability, to be formulated in an aqueous solution, and enable their convenient delivery into the systemic circulation.

17 Claims, 13 Drawing Sheets

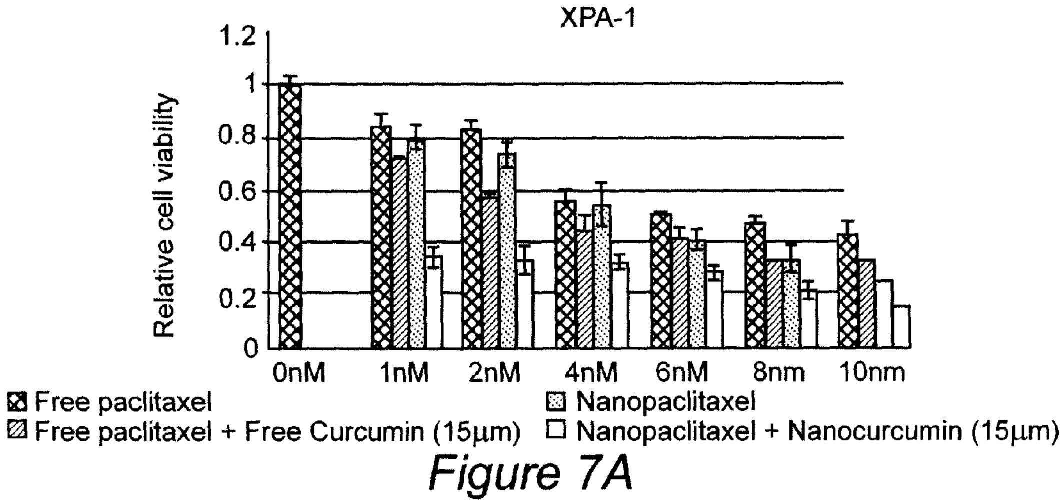
*Figure 7A*
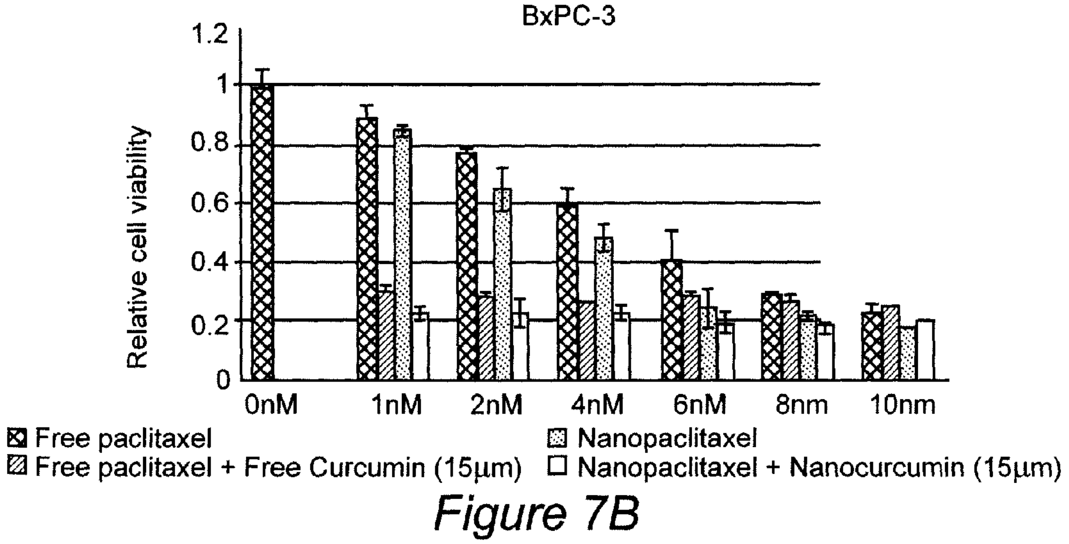
*Figure 7B*
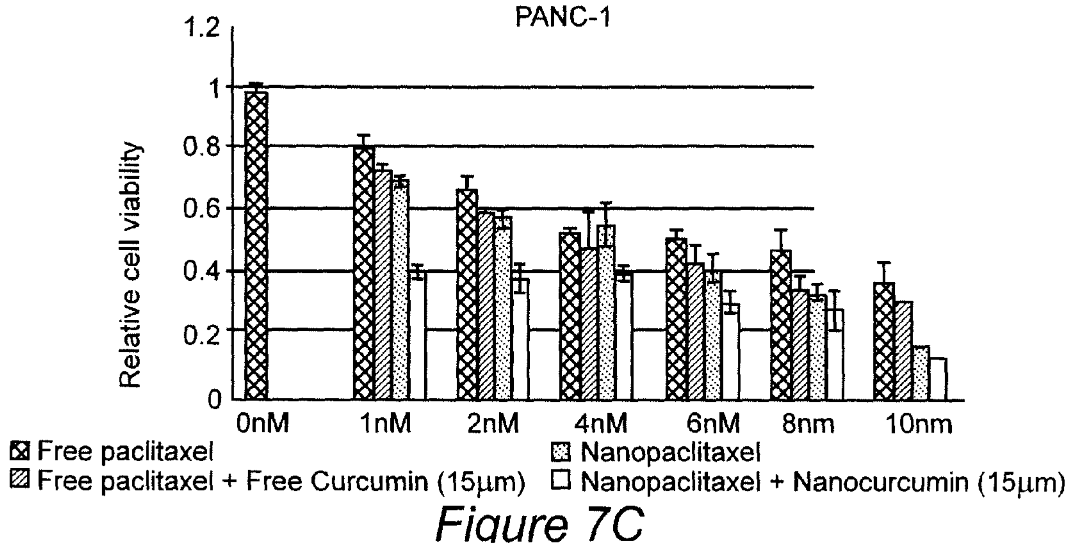
*Fiqure 7C*

WATER-DISPERSIBLE ORAL, PARENTERAL, AND TOPICAL FORMULATIONS FOR POORLY WATER SOLUBLE DRUGS USING SMART POLYMERIC NANOPARTICLES

CROSS-REFERENCE TO RELATED APPLICATIONS

This application claims priority to U.S. Provisional Application Ser. No. 60/849,684 filed Oct. 5, 2006, U.S. Provisional Application Ser. No. 60/866,516 filed Nov. 20, 2006, and U.S. Provisional Application Ser. No. 60/956,760 filed Aug. 20, 2007, and the complete contents of each of these applications is herein incorporated by reference.

FIELD OF THE INVENTION

The invention relates to nanoparticle compositions for solubilization and encapsulation of medicines, including medicines that are poorly water-soluble. More particularly, the invention relates to compositions having 'smart' properties such as mucoadhesivity, oral bioavailability, and multifunctionality for systemic targeting.

BACKGROUND OF THE INVENTION

During the last two decades numerous drug delivery systems have been developed for hydrophobic and poorly water soluble medicines. These systems are focused on overcoming the poor availability of the drug and the subsequent ineffective therapy inherent to these types of molecules.

To solve the above mentioned problem associated with the solubilization of poorly water-soluble medicines, U.S. Pat. Nos. 5,645,856 and 6,096,338 disclose methods for preparing carriers for hydrophobic drugs, and pharmaceutical compositions based thereon, in which the carrier is comprised of biocompatible oil and a pharmaceutically acceptable surfactant component for dispersing the oil in vivo upon administration of the carrier. The amphiphilic surfactant component utilized does not substantially inhibit the in vivo lipolysis of the oil. These types of formulations can be utilized as a carrier system for many hydrophobic drugs resulting sometimes in enhanced bioavailability as compared with existing formulations of such drugs. However, these formulations are not stable in vivo and there is the possibility of drug leakage from the emulsion leading to unnecessary side effects in the body. Moreover, the surfactants used may disrupt the biological membranes causing cytotoxicity. In addition, targeting of a drug using such emulsion systems is not possible.

Other drug carriers have been used such as amphiphilic block copolymers which form polymeric micelles or supramolecular assemblies wherein the hydrophobic part forms the core and the hydrophilic part the shell. The U.S. Pat. No. 5,510,103 describes block copolymers having the hydrophilic and hydrophobic segments forming micelles and entrapping the hydrophobic drugs by physical methods. The hydrophilic segment is preferably poly(ethylene oxide) and the hydrophobic segment is preferably poly(epsilon-benzyl-L-aspartate), while the preferred drug is Adriamycin.

Recently, polymeric micelles have been widely used as drug delivery carriers for parenteral administration. Micellar drug delivery carriers have several advantages including biocompatibility, solubilization of hydrophobic drugs in the core, nanometric size ranges which facilitate extravasation of the drug carrier at the site of inflammation, site-specific delivery, etc. For example, U.S. Pat. No. 5,955,509 describes the use of poly(vinyl-N-heterocycle)-b-poly(alkylene oxide) copolymers in micelles containing pharmaceutical formulations. These copolymers respond to pH changes in the environment and can be used to deliver therapeutic compounds at lower pH values. These polymeric micelles remain intact at physiological pH, while they will release their content when exposed to a lower pH environment such as in tumor tissue.

A number of amphiphilic copolymers, having non-ionic and/or charged hydrophobic and hydrophilic segments, that form micelles are reported in the literature. For example, U.S. Pat. No. 6,322,817 discloses the injectable formulation of cross-linked polymeric micelles constituted by acrylic monomers—N-isopropylacrylamide, N-vinylpyrrolidone and PEGylated monoesters of maleic acid. These polymeric nanoparticles are reported to have dissolved paclitaxel and delivered the drug to the tumor tissue through parenteral administration. However, these particles are only reported to be suitable for delivery via the intravenous route. Moreover, the reported use of alkylcyanoacrylate as one of the components in the copolymeric micelles may render the formulations toxic and unsuitable for in vivo applications.

One patent, U.S. Pat. No. 6,555,139 has disclosed a process of microfluidization or wet-micronization of hydrophobic drugs in combination with dextrins such as β-cyclodextrin. The patent indicated that the process of microfluidization facilitates the reduction of mean particle size of slightly soluble but highly permeable drugs, and creates a smooth, latex-like micro-suspension. A blend of expandable polymer and insoluble, hydrophilic excipients granulated with the micro-suspension create a matrix that after compaction erodes uniformly over a 24-hour period. However, the problems associated with these microfluidization systems are that for every molecule of drug, one molecule of β-cyclodextrin is required leading to large amounts of this compound to be administered inside the body along with drug. Moreover, drug leakage from β-cyclodextrin as well as poor bioavailability of β-cyclodextrin—drug complex has the potential to cause side effects. Finally, the particle size of up to 500 nm diameter may be responsible for limited utility for drug delivery purposes.

Another patent, U.S. Pat. No. 6,579,519 has disclosed the formulation of non-PEGylated pH sensitive and temperature sensitive cross-linked polymeric micelles constituted of N-isopropylacrylamide, acrylic acid and N-vinylpyrrolidone. These particles have extremely limited applications and can be used only for the specific purpose of topical delivery on the ocular surface. This is because of the fact that the LCST (lower critical solution temperature) of the particles is below ambient body temperature, and the particles are aggregated to a hydrophobic mass in vivo. Therefore, these particles are not suitable for systemic circulation and targeting, including oral delivery. Other similar patents are U.S. Pat. No. 6,746,635 and U.S. Pat. No. 6,824,791.

Another U.S. Pat. No. 7,094,810 describes a formulation which is composed of a hydrophilic segment made of poly (ethylene oxide) and a hydrophobic segment composed of vinyl monomers containing at least one pendant carboxyl group. More particularly, the vinyl monomers included in the polymer are acrylic acid or methacrylic acid having pendant carboxyl groups and butyl (alkyl) acrylate where the butyl segment can be a linear or branched chain. Thus, the hydrophobic segment is a mixture of non-ionizable butyl (alkyl) acrylate and ionizable (alkyl) acrylic acid which controls the hydrophobicity of the polymer. The ionizable carboxylic group of the polymer extended towards the surface of the particle is reported to be responsible for pH sensitivity.

Though the majority of these polymers can be used for injectable or topical delivery of bioactive agents, what are presently lacking are multifunctional amphiphilic polymers capable of oral delivery applications, by means of their nanoparticulate size and mucoadhesivity. The surface reactive functional groups of such "smart" nanoparticles would be capable of optional modification through PEGylation, ligand attachment, or fluorophore tagging for the purposes of systemic targeting, thus being useful for concurrent biological applications in diagnostics, therapeutics, and in imaging. Herein, we describe such an orally bioavailable smart polymeric nanoparticle system.

SUMMARY OF THE INVENTION

The invention relates to cross-linked polymeric nanoparticles, which may contain one or more bioactive agents such as poorly water-soluble medicines, and that are particularly suitable for oral delivery, but are also amenable to other applications, including injectable or topical formulations.

A further object of this invention is to provide a process for the preparation of polymeric nanoparticles that can entrap poorly water-soluble drugs, alone or in combination with other bioactive agents, to the maximum extent possible. The polymeric nanoparticles preferably entrap one or more types of medicament. Preferably the polymeric nanoparticles have an average diameter of less than or equal to 50-100 nm, and less than 5% are in excess of 200 nm in diameter.

Another object of this invention is to provide a process for the preparation of nanoparticles having inter-crosslinked polymeric chains so that the release of the entrapped medicine(s) encapsulated in these nanoparticles can be controlled.

Yet another object of this invention is to provide a process for the preparation of nanoparticles incorporating single or combinations of medicines, with the option of chemically conjugating polyethylene glycol (PEG) chains of varying chain length (50-8000 D) at the outer surface of the nanoparticles to reactive moieties on the surface of formed nanoparticles. The PEG chains help the particles to circulate in the blood for a relatively long time, following systemic administration.

Yet another object of this invention is to enable the delivery of otherwise water soluble drugs, but for which oral delivery is currently not an option, by chemically conjugating the drug, or combinations thereof, on the surface of the nanoparticles, which then act as a vehicle for absorption via the oral route so as to enhance the bioavailability of the drug.

Another objective of this invention is to use carboxylic acid, amine or aldehyde derivatives of acrylic compounds or similar vinyl derivatives alone or in combination as monomers during polymerization for rendering multifunctional characteristics of the nanoparticles so as to make 'smart' nanoparticles.

Still another object of this invention is to provide a process for the preparation of polymeric nanoparticles incorporating poorly soluble medicines or combinations of medicines dispersed in aqueous solution which are free from unwanted and toxic materials, such as non-reacted monomers.

Another object of this invention is to provide a process for the preparation of polymeric nanoparticles incorporating poorly water-soluble medicine or combinations of medicines which can be used for in vivo experiments for the purpose of targeting maximum amounts of medicine to a diseased site and only negligible amounts to other tissues, which obviates the disadvantages associated with the prior art. For example, the polymerized micelle complexes contemplated herein can be functionalized with a targeting moiety such as a fluorophore, a dye, a contrasting agent, an antigen, an antibody, an amino acid, or a sugar like glucosamine or related carbohydrate derivatives, through chemical conjugation with the PEG chains associated with the polymeric micelles, such that the complexes could be used, in addition to stated oral formulations, in medical therapeutics, diagnostics and imaging applications requiring targeted delivery to specific cell or tissue types.

A still further object of this invention is to mask the native taste of certain medicaments incorporated in the polymeric micelles by chemically conjugating taste modifying agents to the surface of the micelles so that the formulation is rendered more palatable during oral uptake.

A still further object of this invention is to provide a method for using polymeric nanoparticles incorporating poorly water-soluble medicine or combinations of medicines prepared according to the process of this invention for the treatment of conditions arising out of undesirable pathogenic and anatomic conditions.

According to the invention, medicinal compositions are prepared which comprise polymeric nanoparticles preferably of a size on average of less than 100 nm diameter entrapping at least one poorly water-soluble hydrophobic medicine alone or in combination with one or more additional medicines. These amphiphilic nanoparticles can be made of cross-linked polymers which are mainly composed of the following three constituents added as monomers at specific molar ratios: (1) N-isopropylacrylamide (NIPAAM), plus (2) either a water-soluble vinyl compound like vinyl acetate (VA) or vinyl pyrrolidone (VP), so as to make the particle shell more hydrophilic, or a water-insoluble vinyl derivative such as styrene (ST) or methylmethacrylate (MMA), so as to make the particle core more hydrophobic, plus (3) acrylic acid (AA), which provides surface reactive functional groups. The surface of the nanoparticles can be optionally functionalized using the reactive functional groups provided by AA, including by PEGylation for long circulation in blood, or by addition of other surface reactive groups which can be used for targeting to tissues in vivo for therapeutic, diagnostic, and imaging applications.

BRIEF DESCRIPTION OF THE FIGURES

FIGS. 7*a-c* illustrate in vitro cell viability (MTT) assays performed to demonstrate the synergistic effects of polymeric nanoparticle encapsulated paclitaxel (nanopaclitaxel) and polymeric nanoparticle encapsulated curcumin (nanocurcumin). Three human pancreatic cancer cell lines (XPA-1, BxPC3 and PANC-1) were incubated with increasing concentrations (1, 2, 4, 6, 8 and 10 nm) of either free paclitaxel (black bar) or equivalent amount of nanopaclitaxel (white bar) for 48 hours. In order to test therapeutic synergy with curcumin, the cells were also incubated with either free curcumin (15 μM) plus free paclitaxel (grey bar), or with equivalent amount of nanocurcumin (15 μM) plus nanopaclitaxel (blue bar). As illustrated, the combination of nanopaclitaxel and nanocurcumin demonstrates increased cytotoxicity than either free paclitaxel or nanopaclitaxel alone at any given dose of paclitaxel. Of note, and especially at the lower dosages used in two of the cell lines (XPA-1 and Panc-1), the combination of nanopaclitaxel and nanocurcumin also appears to have better efficacy than the combination of free paclitaxel and free curcumin, likely due to increased intracellular uptake of the nano-encapsulated compounds. At higher dosages, the combination therapy with either free or nano-encapsulated drugs appears to have comparable effects.

DETAILED DESCRIPTION OF THE INVENTION

Figure 1:
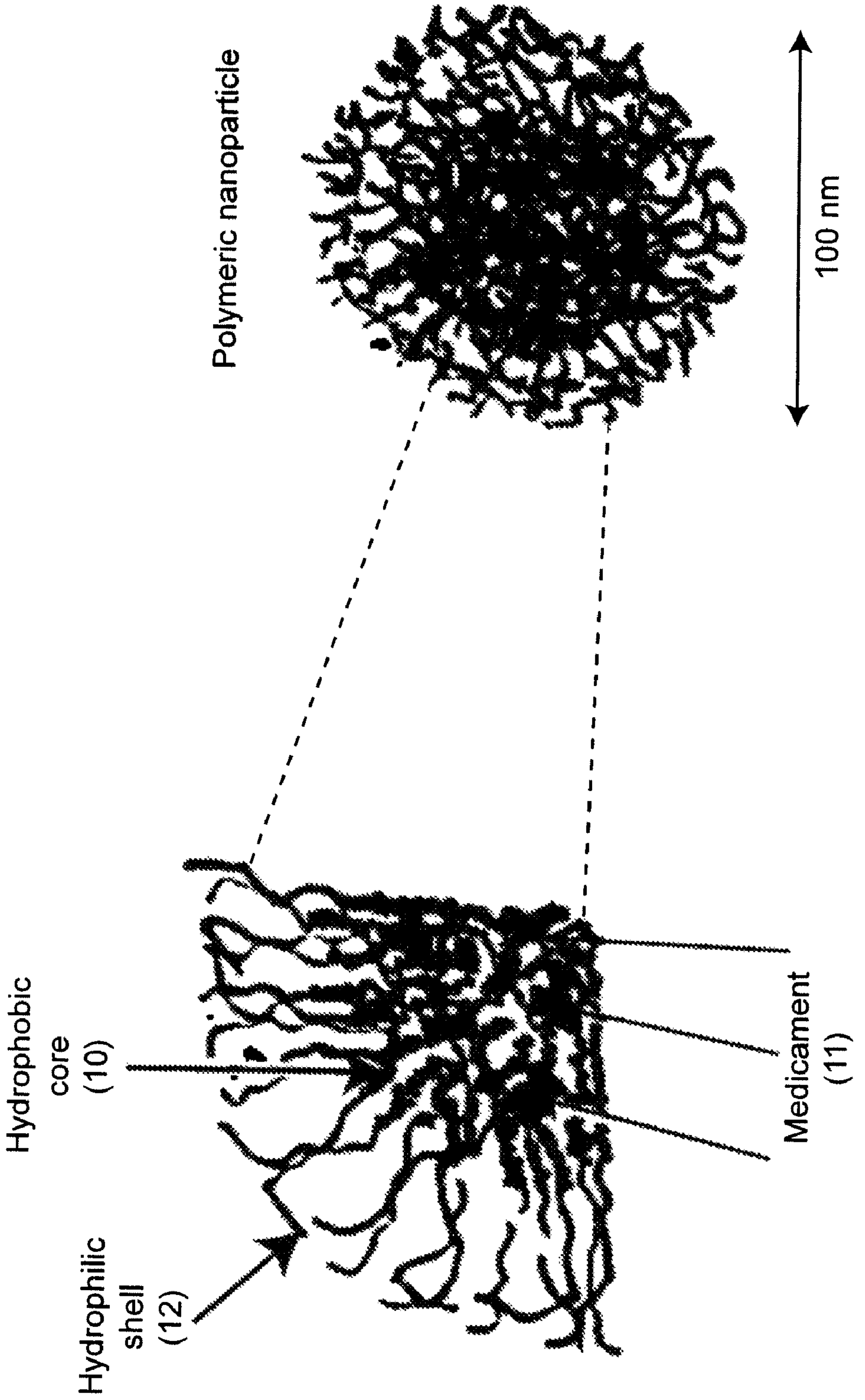
FIG. 1 illustrates a polymeric nanoparticle with the hydrophobic core (10) composed of hydrophobic parts of the polymers entrapping the medicine (11), the hydrophilic parts forming a hydrophilic shell (12) which are present towards the aqueous medium. The nanoparticles are less than 100 nm in size, and may include one or more molecules of medicaments or other bioactive agents.
Figure 2A:
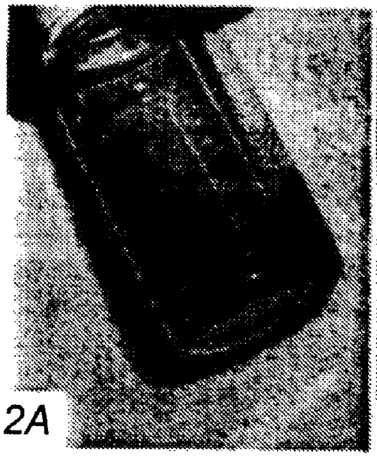
FIGS. 2*a-f* illustrate three examples of poorly water soluble drugs whose solubilization has been enabled by entrapment in polymeric nanoparticles embodied in this invention. Free paclitaxel (taxol) (A), free rapamycin (C), and free rifampicin (E) are essentially insoluble in water, as evidenced by turbidity of solution and visible floating particles of each drug. In contrast, equivalent amounts of nanoparticle-encapsulated paclitaxel (B), nanoparticle-encapsulated rapamycin (D), and nanoparticle-encapsulated rifampicin (F) form transparent solutions in water.
Figure 2B:
Figure 2C:
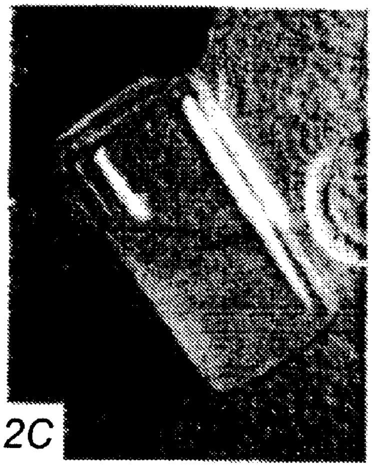
Figure 2D:
Figure 2E:
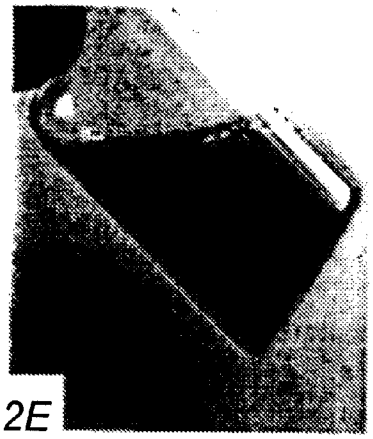
Figure 2F:

Medicinal compositions of poorly water-soluble medicines, alone or in combination with two or more medicines, entrapped into polymeric nanoparticles are described herein. Medicinal composition of water-soluble medicines such as gemcitabine conjugated to a surface of polymeric nanoparticles are also described herein. After formation, the nanoparticles are approximately spherical and preferably have a size that averages 50-100 nm or less in diameter. The nanoparticles may be described as nanometer sized particles of micellar aggregates of amphiphilic and cross-linked polymers.

In the present invention, nanoparticles of polymeric micelles are prepared by:

(i) dissolving NIPAAM and AA in water to form micelles, (ii) adding at least one compound of vinyl derivative, which may be either water-soluble or insoluble in water, but both are soluble in the said micelles and which can be polymerized through free radical polymerization, (iii) adding appropriate amount of activator and initiator, which are, for example, tetramethylethylene diamine (TMED) and ferrous ammonium sulphate. As activators and ammonium perdisulphate as activator.

(iv) adding a cross-linking agent to the said micellar solution, which is preferably N,N' methylene bis acrylamide (v) polymerizing the monomers into copolymer in presence of an inert gas such as nitrogen at 30 C to 40 C temperature for 24 hours for nearly completion of the reaction, (vi) purifying the nanoparticles of the co-polymeric micelles by dialysis for three hours to remove toxic monomers and other unreacted materials, (vii) optional surface modification of the nanoparticles by chemically conjugating PEG amine of variable chain length (50-8000 D) or other conjugated moieties to reactive functional groups on the nanoparticle surface, (viii) addition of one or more bioactive agents for entrapment within the formed polymeric nanoparticles in aqueous solution, or lyophilizing the empty polymeric nanoparticles to dry powder for future use, (ix) reconstituting the dry powder of empty polymeric nanoparticles in an aqueous solution, and addition of one or more bioactive agents for entrapment within the said polymeric nanoparticles, (x) lyophilizing the drug-loaded polymeric nanoparticles to dry powder, and (xi) reconstituting the drug loaded polymeric nanoparticles in aqueous solution for oral, injectable, or topical delivery.

Besides NIPAAM and AA, the vinyl monomers are selected from water soluble vinyl compounds such as vinyl acetate, 4-vinyl benzoic acid, N-vinylpyrrolidone (VP), and N-vinyl piperidone, while water insoluble amphiphilic vinyl compounds include methylmethacrylate (MMA), vinylmethacrylate, N-vinyl caprolactum, N-vinyl carbazole, and styrene.

In one embodiment, the nanoparticles are formed by polymerization of the monomers in the reaction mixture. The compositions are in the following molar ratios: NIPAAM, about 50% to about 90%, and preferably 60% for specific delivery routes such as oral or parenteral; a vinyl monomer like the water-soluble VP or water-insoluble MMA, about 10% to about 30%; and AA, about 10% to about 30%. The monomers are dissolved in water and ammonium perdisulphate TEMED and ferrous ammonium sulphate are added to it. N,N' methylene bis acrylamide is also added to cross-linked the polymer. The mixture is permitted to polymerize, preferably in the presence of an inert gas (e.g., nitrogen, argon, etc.), at a temperature preferably ranging from 20° C. to 80° C., or more preferably from 30° C. to 40° C., until polymerization is complete. Completion of polymerization may be determined by depletion of monomers from the reaction mixture by HPLC or $^{1}$H NMR of vinyl protons. The solution may be purified by dialysis, for example for 2-4 hours, to remove any toxic monomers or other unreacted species. In Example 1, NIPAAM, VP, and AA were used to prepare copolymers with the molar ratios of 60:30:10, 60:20:20, and 60:10:30, in order to potentially modulate the mucoadhesivity of orally delivered nanoparticles in the GI tract by varying the proportion of AA in the polymer. In Example 2, similar co-polymeric nanoparticles were prepared in which VP has been replaced by MMA, and in the specific example the molar ratios used was 60:20:20 for NIPAAM, MMA and AA, respectively. As will be discussed below, the proportion of monomers utilized also affects stability of the nanoparticles at body temperature.

One embodiment of the invention is illustrated in FIG. 1, which shows that the nanoparticles have a hydrophobic core (labeled 10) composed of hydrophobic parts of the polymers entrapping the medicine (labeled 11), whereas the hydrophilic parts forming a hydrophilic shell (labeled 12) are present towards the aqueous medium. As also shown in FIG. 1, the polymeric nanoparticles are preferably less than 100 nm in size, and may include one or more molecules of medicaments or other bioactive agents.

Figure 3:
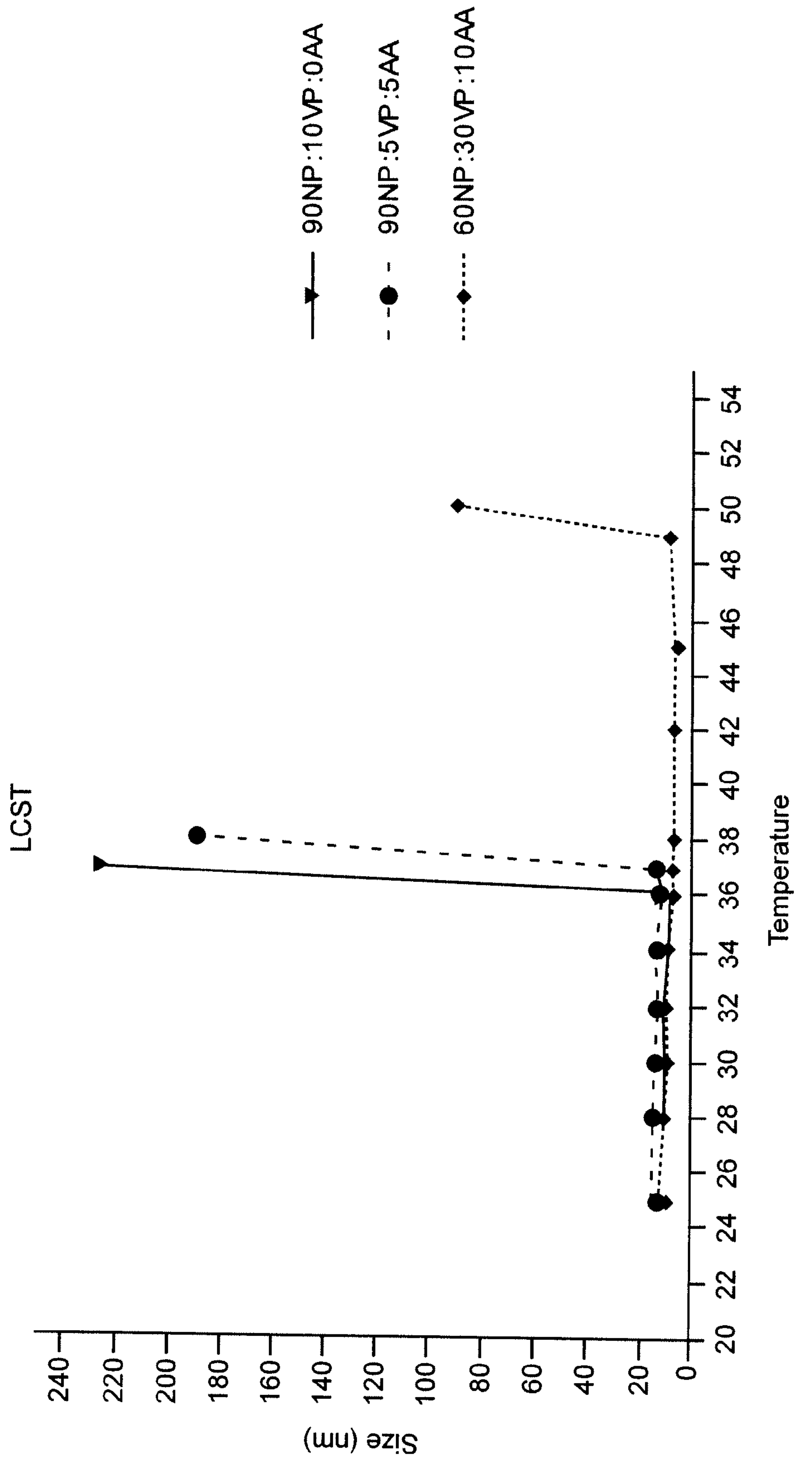
FIG. 3 shows lower critical solution temperature (LCST) as a function of the weight percent ratio of the constituents, and in particular the molar ratio of NIPAAM in the nanoparticles. In the illustrated example, three different compositions of nanoparticles are represented, each with a different molar ratio of NIPAAM (NP), vinyl pyrrolidone (VP) and acrylic acid (AA) comprising the polymeric nanoparticles. Average size of nanoparticles (nm) is measured by dynamic light scattering and other methods. Compositions with a NIPAAM molar ratio of 90% have a LCST below that of body temperature, while compositions with a NIPAAM molar ratio of 60% has a LCST above that of body temperature.
Figure 4A:
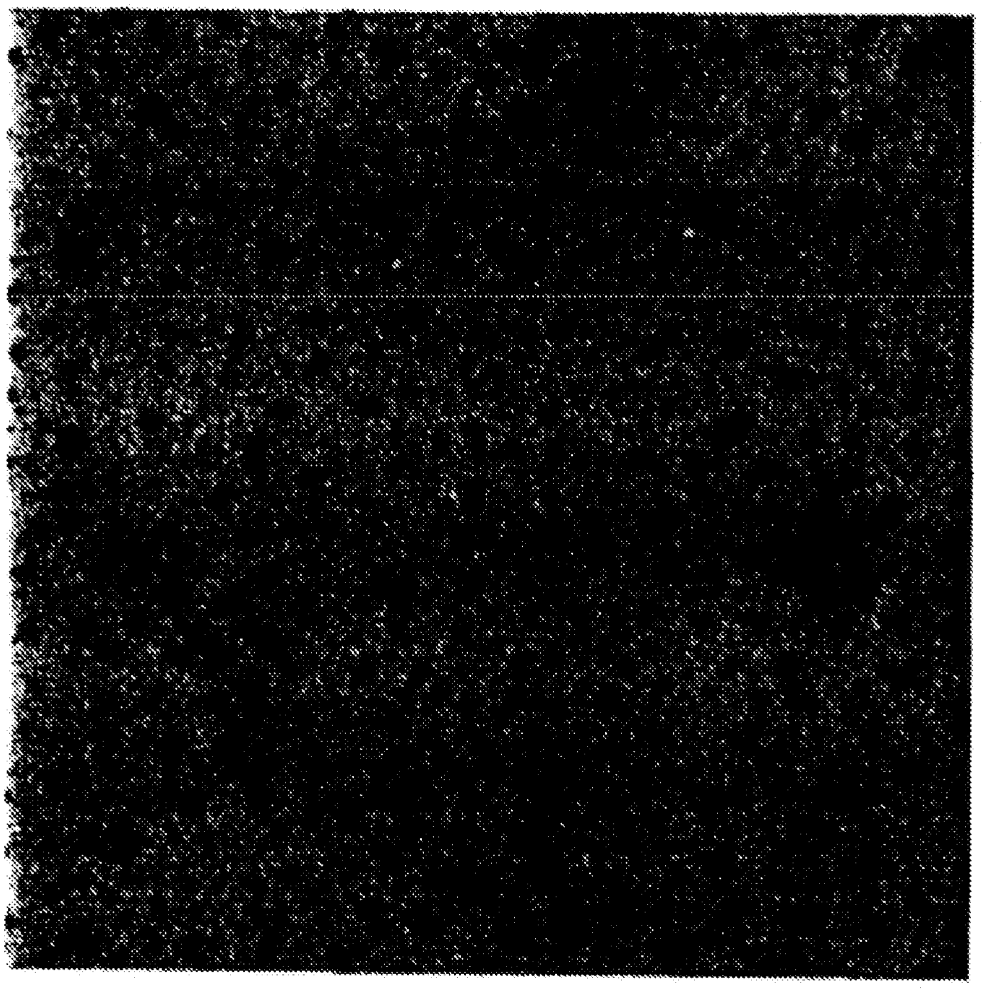
FIG. 4*a* is a Transmission Electron Microscopy (TEM) photomicrograph of NIPAAM/VP/AA polymeric nanoparticles (molar ratios of 60:20:20), which have an average diameter of 50 nm or less (100 nm scale is illustrated at bottom right).
Figure 4B:
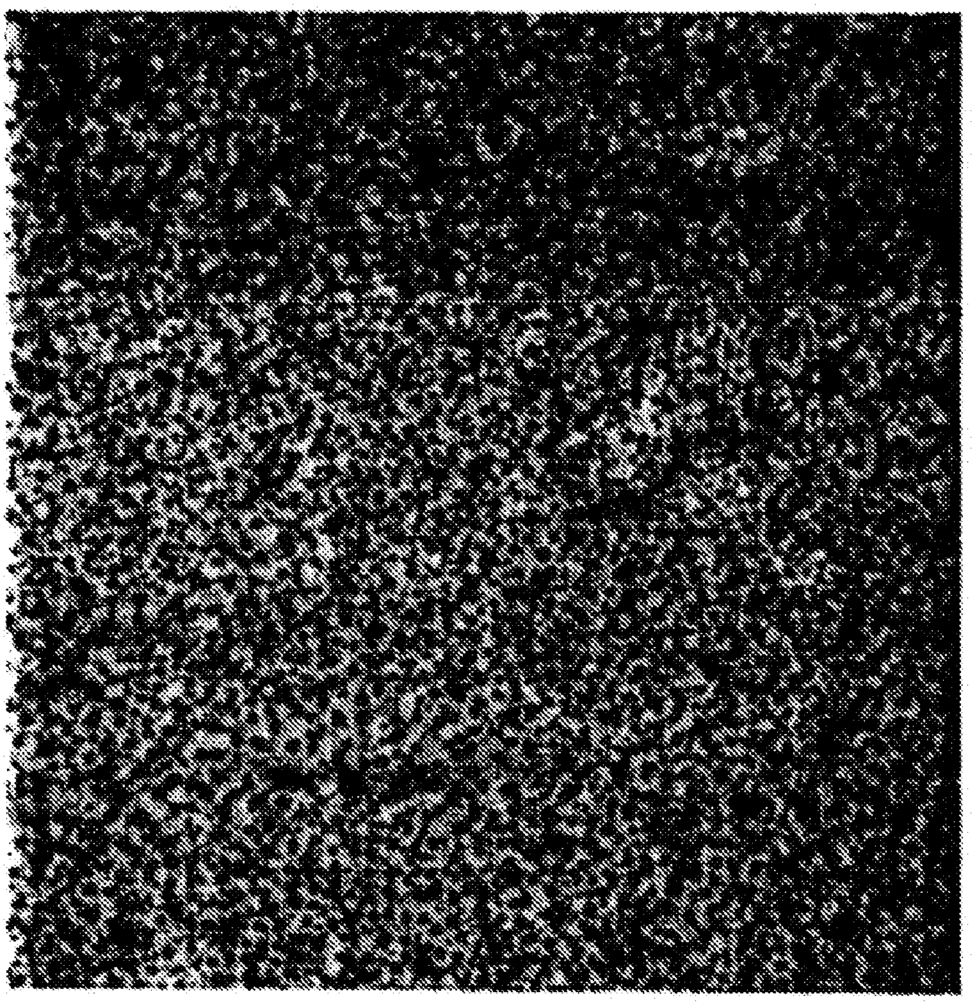
FIG. 4*b* is a TEM photomicrograph of NIPAAM/MMA/AA polymeric nanoparticles (molar ratios of 60:20:20), which have an average diameter of 50 nm or less (500 nm scale is illustrated at bottom right). Minimal polydispersity is observed.
Figure 5:
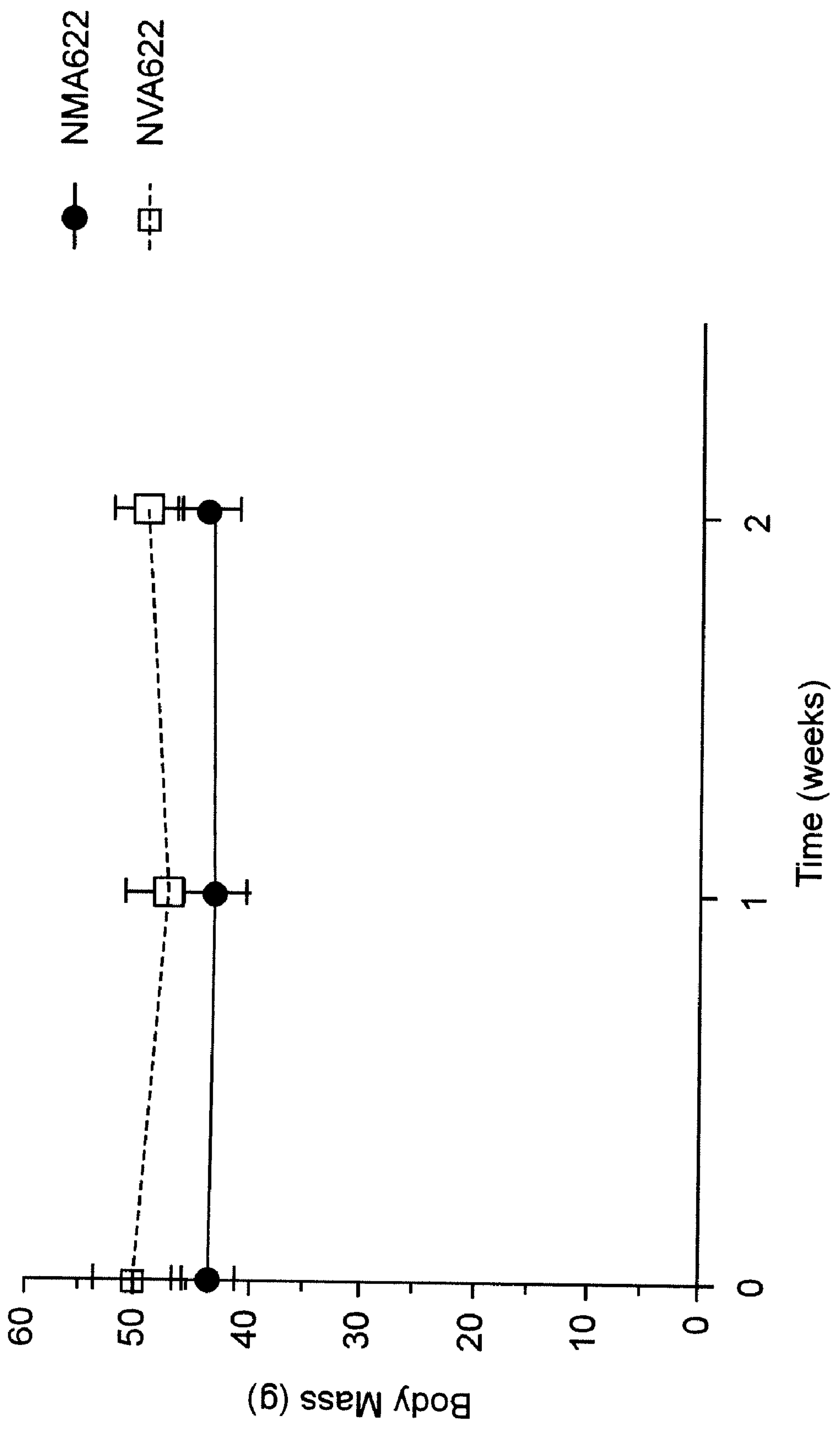
FIG. 5 illustrates lack of demonstrable in vivo toxicity from orally delivered empty ("void") polymeric nanoparticles. Two types of orally delivered void nanoparticles were utilized: NIPAAM/VP/AA in molar ratios of 60:20:20 (designated NVA622) and NIPAAM/MMA/AA in molar ratios of 60:20:20 (designated NMA622). Groups of four CD1 wild type mice each (two males, two females) were administered 500 mg/kg of void NVA622 or void NMA622 nanoparticles in 500 μL of water, five consecutive days a week, for two weeks. During and at the culmination of void nanoparticle administration, no weight loss, behavioral abnormalities or other abnormal features were seen. No gross (macroscopic) toxicities were observed in the mice receiving either the void NVA622 or the void NMA622 nanoparticles.

Due to the presence of NIPAAM in the copolymeric formulation, the nanoparticle shell is converted from a hydrophilic to a hydrophobic entity at the lower critical solution temperature (LCST), which can be modulated by changing the amount of NIPAAM in the proportion of monomers used, as seen in FIG. 3. To render these nanoparticles suitable for systemic circulation, the nanoparticles should have a LCST above human body temperature (~37° C.). In order to obtain a high LCST of the nanoparticles, i.e., in the 45-50° C. range, enabling systemic medicine delivery and stability of the nanoparticles at body temperature, it is required that the NIPAAM component be used in an optimum molar ratio of 50-70%, with the two remaining monomers comprising the remaining 100%. As noted above, additional monomers or functional moieties may also be included, and these do not impact the LCST.

Figure 10:
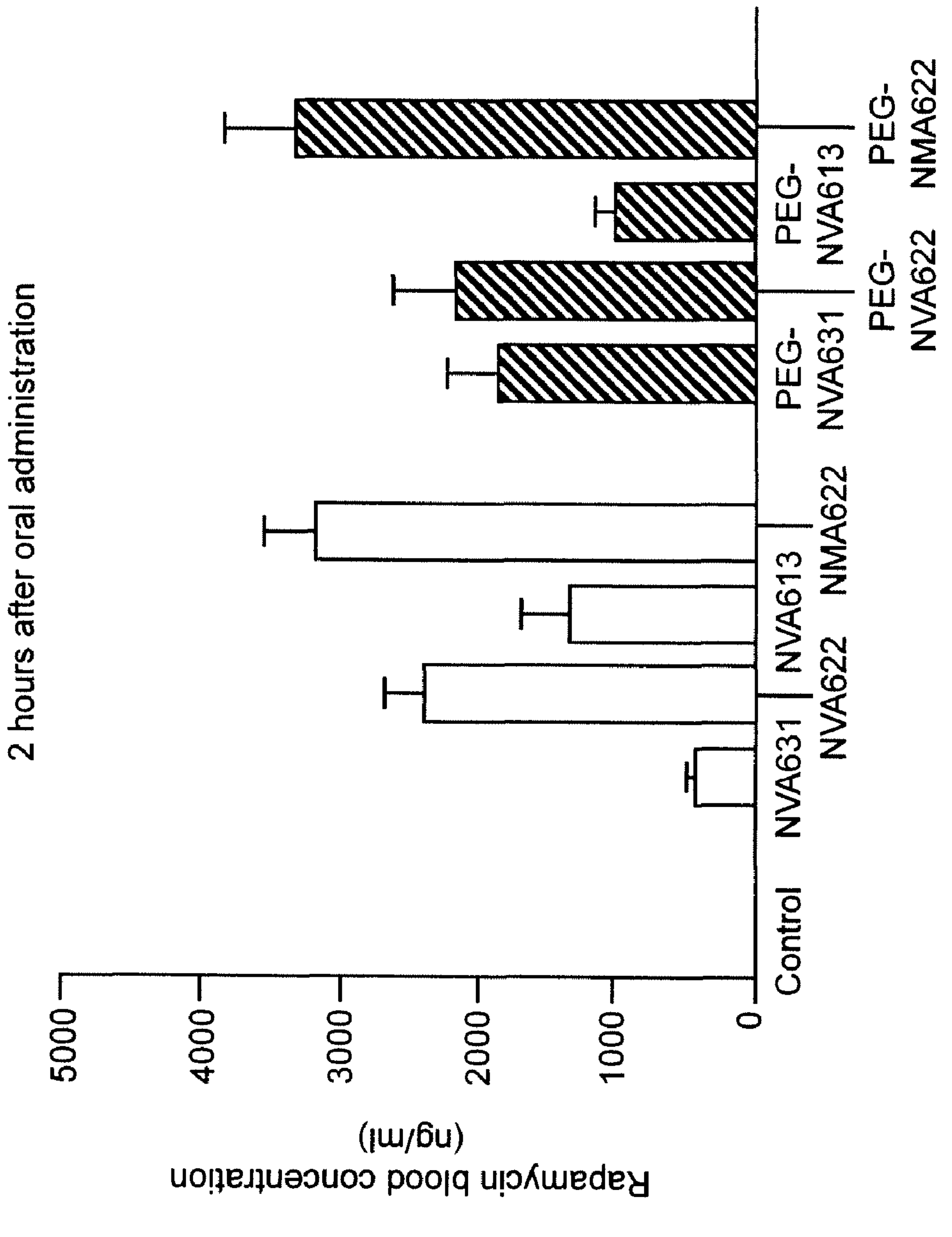
FIG. 10 illustrates blood levels of rapamycin following oral delivery of polymeric nanoparticles. Rapamycin was encapsulated in nanoparticles comprised of increasing order of acrylic acid (AA) percentage in the co-polymeric composition. The nanoparticles were either administered as is, or after surface PEGylation. Compared are: Control A (rapamycin suspended in water); rapamycin nanoparticle comprised of NIPAAM:VP:AA in a ratio of 60:30:10 (designated as NVA631); rapamycin nanoparticle comprised of NIPAAM:VP:AA in a ratio of 60:20:20 (designated as NVA622); rapamycin nanoparticle comprised of NIPAAM:VP:AA in a ratio of 60:10:30 (designated as NVA613); and rapamycin nanoparticle comprised of NIPAAM:MMA:AA in a ratio of 60:20:20 (designated as NMA622). The corresponding PEGylated nanoparticles (PEG-NVA-631, PEG-NVA-622, PEG-NVA-613, and PEG-NMA-622) encapsulating rapamycin are designated as shaded bars. Rapamycin was administered either as free drug dispersed in water (15 mg/kg) or as equivalent dosage of nano-encapsulated rapamycin in the respective polymeric nanoparticle formulation. Six wild type C57/B6 mice were included in each arm of this study. Blood levels are measured by HPLC from samples obtained at 2 hours post oral delivery. Two types of nanoparticles, each containing 20% molar ratio of AA (NVA622 and NMA622) demonstrate highest blood levels of rapamycin following oral delivery.

The nanoparticles described herein can be used as is for drug delivery, or optionally, the surface of nanoparticles may be modified by functionalizing reactive surface groups (COO—) provided by AA for attachment of PEG amine chains of variable length (50-8000 D), or for the chemical conjugation of targeting moieties like ligands, antibodies, radionuclides, fluorophores, and contrast agents, or for the addition of taste masking agents like aspartame. The addition of PEG amine chains does not impede the observed oral bioavailability of the drug encapsulated nanoparticles, as seen in FIG. 10. Herein, four independent nanoparticle formulations encapsulating rapamycin (NVA631, NVA622, NVA613, and NMA622) were administered to mice via oral route, and the drug levels at two hours in the systemic circulation compared with that of rapamycin encapsulated in corresponding PEGylated nanoparticles (PEG-NVA613, PEG-NVA622, PEG-NVA613, and PEG-NMA622). As seen, the blood levels of rapamycin following oral delivery of non-PEGylated and PEGylated nanoparticles are comparable. Those skilled in the art will be aware that PEGylation renders nanoparticle long circulating, by evading the innate reticuloendothelial system (RES), and the engineering of "RES evading" nanoparticles embodied in this invention does not impede their oral bioavailability.

The polymeric nanoparticles disclosed herein are preferably loaded with medicines or other bioactive agents to the maximum extent possible. The medicines or bioactive agents can be organic compounds that are poorly soluble or insoluble in water but readily soluble in organic solvents. The medicine or bioactive agent is added to the polymeric solution either in the form of dry powder or as a solution in chloroform, ethanol or ether depending on the solubility of the drug in that solvent to form an optically clear solution. Examples of such medicines include, but are not limited to, antineoplastic agents such as Paclitaxel, Docetaxel, Rapamycin, Doxorubicin, Daunorubicin, Idarubicin, Epirubicin, Capecitabine, Mitomycin C, Amsacrine, Busulfan, Tretinoin, Etoposide, Chlorambucil, Chlormethine, Melphalan, and Benzylphenylurea (BPU) compounds; phytochemicals and other natural compounds such as curcumin, curcuminoids, and other flavinoids; steroidal compounds such as natural and synthetic steroids, and steroid derivatives like cyclopamine; antiviral agents such as Aciclovir, Indinavir, Lamivudine, Stavudine, Nevirapine, Ritonavir, Ganciclovir, Saquinavir, Lopinavir, Nelfinavir; antifungal agents such as Itraconazole, Ketoconazole, Miconazole, Oxiconazole, Sertaconazole, Amphotericin B, and Griseofulvin; antibacterial agents such as quinolones including Ciprofloxacin, Ofloxacin, Moxifloxacin, Methoxyfloxacin, Pefloxacin, Norfloxacin, Sparfloxacin, Temafloxacin, Levofloxacin, Lomefloxacin, Cinoxacin; antibacterial agents such as penicillins including Cloxacillin, Benzylpenicillin, Phenylmethoxypenicillin; antibacterial agents such as aminoglycosides including Erythromycin and other macrolides; antitubercular agents such as rifampicin and rifapentin; and anti-inflammatory agents such as Ibuprofen, Indomethacin, Ketoprofen, Naproxen, Oxaprozin, Piroxicam, Sulindac. Preferably, the medicine(s) loaded in the compositions range from 1% to 20% (w/w) of the polymer; however, in some applications the loading may be considerably higher.

Figure 11:
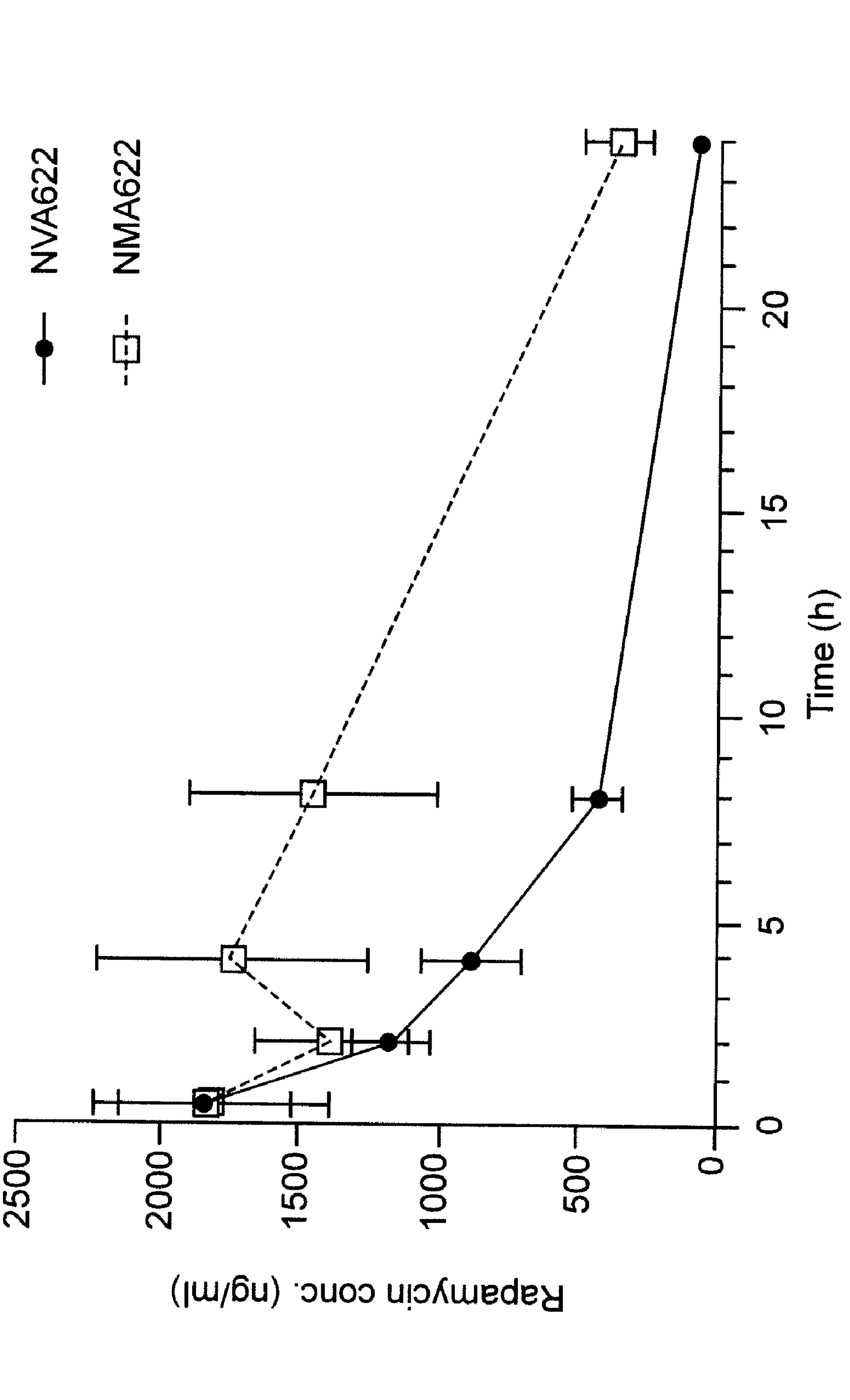
FIG. 11 illustrates pharmacokinetic (PK) data of orally delivered nano-encapsulated rapamycin in mice, over a 24 hour period. Two polymeric nanoparticle formulations with highest blood levels at 2 hours (FIG. 10) were selected for this study: NVA622 and NMA622, containing NIPAAM/VP/AA and NIPAAM/MMA/AA in 60:20:20 molar ratios, respectively. Six wild type C57/B6 mice were included in each arm of the study. Single dose of nano-encapsulated rapamycin (equivalent to 15 mg/kg of drug) was administered at time zero, and blood obtained from the facial vein by venupuncture, at 30 minutes, 2, 4, 8, and 24 hours post oral administration. Rapamycin levels were measured by HPLC on mouse plasma. The means and standard deviations (error bars) are plotted for each time point for each of the nanoparticle formulations. NMA622 nanoparticles have a higher area-under-the-curve (AUC) compared with NVA622 nanoparticles (Mean AUC 26,949 versus 11,684, respectively).
Figure 12:
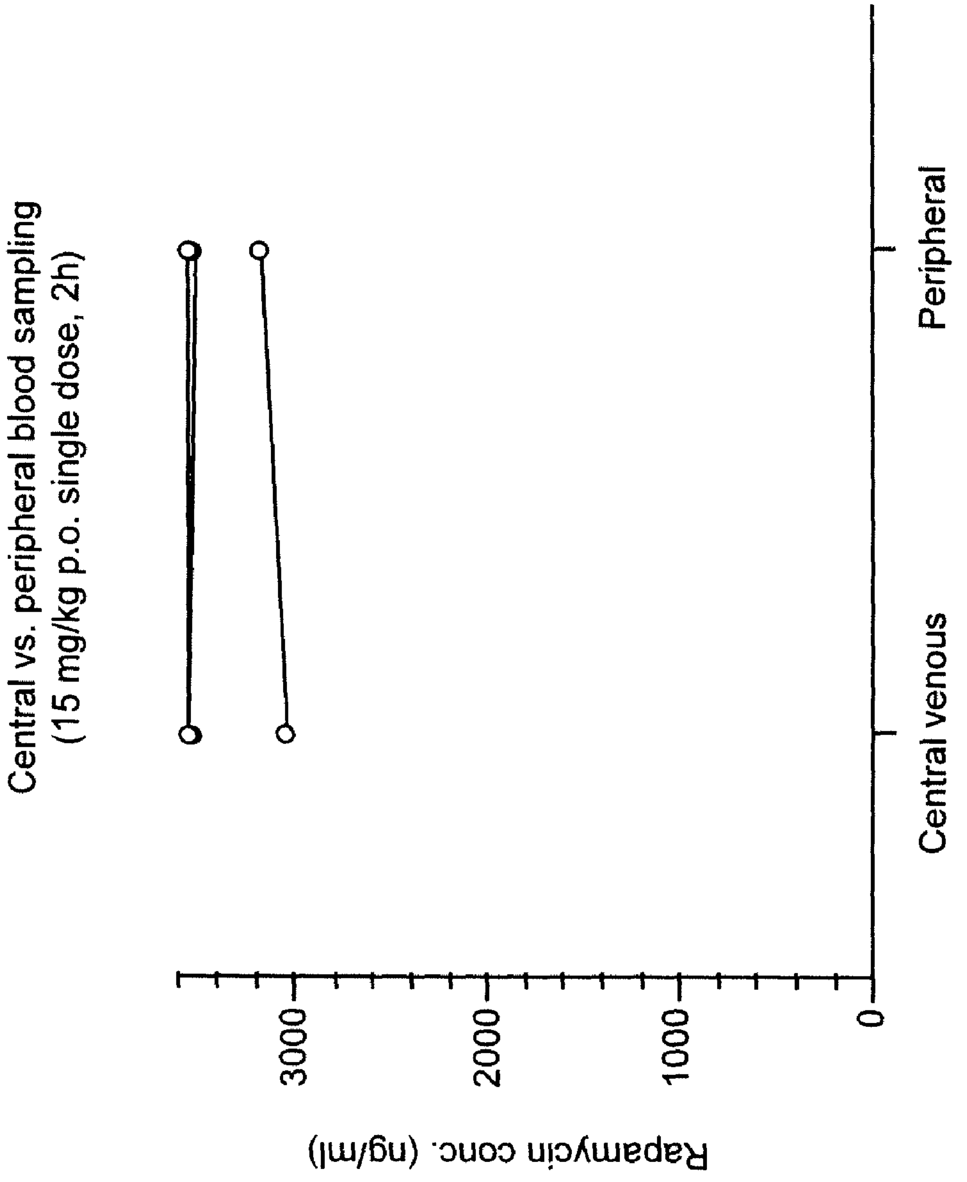
FIG. 12 illustrates levels of rapamycin in central and peripheral venous circulation at 2 hours post-administration of nanoparticle encapsulated rapamycin via oral route. NVA622 particles encapsulating rapamycin were administered via oral route in three mice (dose of 15 mg/kg) and rapamycin levels measured in central venous and peripheral venous (facial vein) circulation at 2 hours. The levels are identical in all three independent measurements between the two sites, consistent with equitable systemic distribution of the orally delivered nanoparticle-encapsulated rapamycin within the blood circulation.

Generally, one or more bioactive agents, such as medicines which are poorly soluble in aqueous media but also including other agents that produce a biological effect, are dissolved in a suitable solvent, such as ethanol or chloroform, and added to a nanoparticle solution. This addition step can be performed before or after nanoparticle formation. Combining the medicines or bioactive agents with the nanoparticle solution results in the entrapment of the medicines or bioactive agents within the hydrophobic core (interior) of the nanoparticles. The nanoparticles containing the entrapped medicines or bioactive agents may, if desired, be lyophilized or otherwise rendered into powder form for subsequent reconstitution in a suitable fluid vehicle for human or mammalian administration. In the subsequently discussed Example 5, incorporating FIGS. 10, 11, and 12, the in vivo oral bioavailability of rapamycin encapsulated in polymeric nanoparticles is demonstrated.

In another embodiment of this invention, a medication, which is water soluble but otherwise has low bioavailability through the oral route, can be attached to the surface of the nanoparticles by covalent conjugation between the reactive carboxylic groups in the nanoparticle and complementary functional groups, such as amine or thiol groups, on the medication. Conjugation to the nanoparticles allows such medications to become orally bioavailable. Examples of such compounds include, but are not limited to, anti-neoplastic agents like gemcitabine.

The nanoparticles containing at least one medicine or a combination of medicines and bioactive agents prepared by the above described process (e.g., nanoparticles with entrapped medicines or medicines conjugated to a surface, or even combinations of both) may be used for the treatment of pathological conditions arising out of various diseases including but not limited to cancer, inflammation, infection and neurodegeneration.

The invention will now be described with reference to the following non-limiting examples:

EXAMPLES

Example 1

Synthesis of Cross-Linked Copolymeric Micelles of NIPAAM, VP (a Water-Soluble Vinyl Derivative), and AA A co-polymer of NIPAAM with VP and AA was synthesized through free radical polymerization. Water-soluble monomers, NIPAAM, VP and AA were dissolved in water in 60:30:10 molar ratios for NVA631, 60:20:20 for NVA622, and 60:10:30 for NVA613. The polymerization was initiated using ammonium persulphate (APS) as initiator in $N_2$ atmosphere. Ferrous Ammonium Sulphate (FAS) was added to activate the polymerization reaction and also to ensure complete polymerization of the monomers to obtain a good yield. Using NVA631 as a prototypal example, in a typical experimental protocol, 62.8 mg of re-crystallized NIPAAM, 30.5 μl of freshly distilled VP and 6.61 μl of AA (freshly distilled) in 10 ml of water were used. To cross-link the polymer chain, 30 μl of MBA (0.049 g/ml) was added in the aqueous solution of monomers. Dissolved oxygen was removed by passing nitrogen gas for 30 minutes. 20 μl of FAS (0.5% w/v), 30 μl of APS and 20 μl of TEMED were then added to initiate the polymerization reaction. The polymerization was carried out at 30° C. for 24 hours in a nitrogen atmosphere. After the polymerization was complete, the total aqueous solution of polymer was dialyzed overnight using a spectrapore membrane dialysis bag (12 kD cut off). The dialyzed solution was then lyophilized immediately to obtain a dry powder for subsequent use, which is easily re-dispersible in aqueous buffer. The yield of the polymeric nanoparticle was more than 90%. When VP is replaced by other water-soluble vinyl derivatives like vinyl alcohol (VA), the method of preparation remains the same, and the co-polymer does not change in its properties.

Example 2

Synthesis of Cross-Linked Copolymeric Micelles of NIPAAM, MMA (Water-Insoluble Vinyl Derivative), and AA A co-polymer of NIPAAM with MMA and AA was synthesized through free radical polymerization. Water-soluble monomers—NIPAAM and AA—were dissolved in water, and water-insoluble MMA was dissolved in the micellar solution of NIPAAM and AA, in 60:30:10 molar ratios for NMA631, 60:20:20 for NMA622, and 60:10:30 for NMA613. The polymerization was initiated using ammonium persulphate (APS) as initiator in $N_2$ atmosphere. Ferrous Ammonium Sulphate (FAS) was added to activate the polymerization reaction and also to ensure complete polymerization of the monomers to obtain a good yield. Using NMA622 as a prototypal example, in a typical experimental protocol for preparing NMA622, 66.6 mg of re-crystallized NIPAAM, 19.4 μl of freshly distilled MMA and 14 μl of AA (freshly distilled) in 10 ml of water were used. To cross-link the polymer chain, 30 μl of MBA (0.049 g/ml) was added in the aqueous solution of monomers. Dissolved oxygen was removed by passing nitrogen gas for 30 minutes. 20 μl of FAS (0.5% w/v), 30 μl of APS and 20 μl of TEMED were then added to initiate the polymerization reaction. The polymerization was carried out at 30° C. for 24 hours in a nitrogen atmosphere. After the polymerization was complete, the total aqueous solution of polymer was dialyzed overnight using a spectrapore membrane dialysis bag (12 kD cut off). The dialyzed solution was then lyophilized immediately to obtain a dry powder for subsequent use, which is easily re-dispersible in aqueous buffer. The yield of the polymeric nanoparticle was more than 90%. When MMA is replaced by other water insoluble vinyl derivatives like styrene (ST), the method of preparation remains the same, and the co-polymer does not change in its properties

Example 3

Surface Modification of NIPAAM VP/AA Copolymeric Micelles with 5 kD PEG Moiety The formulations NVA631, NVA622 or NVA613 were prepared using the detailed protocol as described above. The exemplary functionalized PEG molecule used for post-copolymerization conjugation to AA was Methoxy-polyethylene glycol amine (Methoxy-PEGamine; molecular weight 5000 D). Conjugation of Methoxy-PEGamine with the carboxylic group of acrylic acid in the co-polymer was done by using EDCI as a crossslinker. Briefly, 100 mg of the lyophilized co-polymer powder was dissolved in 10 ml of phosphate buffer. To this, 5 mM of 1-ethyl-3-(3-dimethylaminopropyl)-carbodiimide hydrochloride (EDCI) was added and stirred for 30 minutes. Thereafter, 5 mg of Methoxy-PEGamine was added to the copolymer solution and stirred overnight at room temperature. The next day, the solution was dialyzed for 2-4 hrs to remove any unconjugated Methoxy-PEGamine using a 12 kD dialysis membrane followed by subsequent lyophilization. The resulting nanoparticles are designated as PEG-NVA631, PEG-NVA-622, and PEG-NVA613. Identical PEGylation can be performed with the NIPAAM/MMA/AA formulations, and are designated PEG-NMA631, PEG-NMA622, and PEG-NMA613, respectively.

Example 4

Preparation of Polymeric Nanoparticles Encapsulating the Poorly Water Soluble Immunomodulatory and Anti-Cancer Drug, Rapamycin The immunomodulatory and anti-cancer agent rapamycin is known to be poorly absorbed when administered through the oral route. To study the delivery of rapamycin using the nanoparticles of the invention, rapamycin was incorporated into NVA631, NVA622, NVA613, and NMA622 nanoparticles, or the respective PEGylated derivatives (PEG-NVA631, PEG-NVA622, PEG-NVA613 and PEG-NMA622) as follows: 100 mg of lyophilized dry powder of the respective nanoparticle was dispersed in 10 ml distilled water and was stirred well to reconstitute the micelles. The free drug rapamycin was dissolved in chloroform (10 mg/ml) and the drug solution in $CHCl_3$ was added to the polymeric solution slowly with constant vortexing and mild sonication. Rapamycin was directly loaded into the hydrophobic core of micelles. The drug-loaded micelles were then lyophilized to dry powder for subsequent use. Up to 3 mg of rapamycin per 100 mg of micellar powder was entrapped in each of the co-polymeric micelles (NVA631, NVA622, NVA613, and NMA622 and the respective PEGylated derivatives) to form a drug loaded nanoparticle solution, thus giving a total loading of 3% (w/w) of the polymer.

This example shows that poorly water soluble drugs can be easily and efficiently loaded into the nanoparticles of the invention.

Example 5

In Vivo Oral Administration of Polymeric Nanoparticles Encapsulating Rapamycin Rapamycin is a poorly water soluble drug that has low oral bioavailability. The objective of these experiments was to determine whether nano-encapsulation of rapamycin in the polymeric nanoparticles embodied in this invention can enhance absorption upon oral administration, compared to free rapamycin in aqueous media. Nine independent sets of C57B6 wild type mice (N=6 mice per set) were studied. Rapamycin was administered to the mice as oral free rapamycin (15 mg/kg body weight) suspended in water, or the equivalent amount of rapamycin encapsulated in NVA631, NVA622, NVA613 and NMA622 nanoparticles, or the respective surface modified PEGylated derivatives. All dosages were given by oral lavage. At 2 hours post oral administration, the mice were bled and rapamycin concentrations in the blood were determined by high performance liquid chromatography (HPLC). The results of this study are presented in FIG. 10. As can be seen, all nanoparticles tested successfully delivered high levels of rapamycin to the blood stream compared to free rapamycin in water, which was essentially undetectable. We ascribe these high systemic levels following oral delivery to both the nanoparticulate size (~50 nm in diameter) of the carrier polymers, as well as their enhanced gastrointestinal mucoadhesivity due to the availability of free COO— (carboxyl) groups on the surface from the AA component in the polymer. Further, two of the nanoparticle formulations, NVA622 and NM622, had the highest two-hour blood levels, which we ascribe to an optimum molar ratio of mucoadhesive AA in the polymeric composition. This study also demonstrates that partial PEGylation of AA (as present in PEG-NVA631, PEG-NVA622, PEG-NVA613, and PEG-NMA622) does not impede the mucoadhesive tendencies of the nanoparticles, likely because a sufficient number of free COO— groups are available for mucosal adhesion even after the PEGylation. Therefore, the optional PEGylation of these nanoparticles, as sometimes required for long systemic circulation, does not impede oral bioavailability. The experiment in FIG. 11 confirms the rapid and robust oral uptake of the nanoparticle-encapsulated drug, with markedly high levels observed as early as 30 minutes after oral administration. Finally, the experiment in FIG. 12 confirms the equitable systemic distribution of the nanoparticle encapsulated drug in the circulation following their oral delivery, with near-identical levels of rapamycin observed in central and peripheral circulatory compartments. Thus, this example demonstrates the ability of polymeric nanoparticles embodied in this invention to efficiently deliver one or more encapsulated poorly water soluble drugs to the systemic circulation via the oral route.

Example 6

Figure 6A:
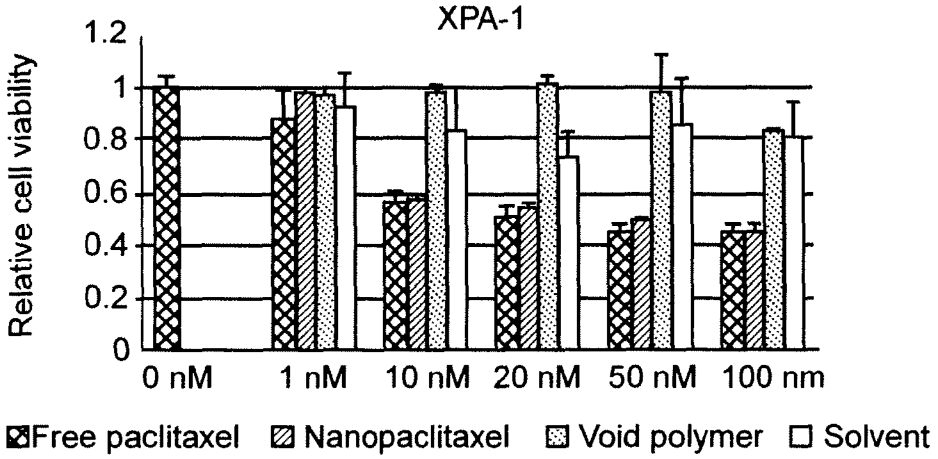
FIGS. 6*a-c* illustrate in vitro cell viability (3-(4,5-Dimethylthiazol-2-yl)-2,5-diphenyltetrazolium bromide, or MTT) assays performed with polymeric nanoparticle encapsulated paclitaxel (nanopaclitaxel), and comparison with free paclitaxel. In the illustrated example, NIPAAM/VP/AA polymeric nanoparticles in molar ratio of 60:20:20 were used for paclitaxel encapsulation. Three human pancreatic cancer cell lines (XPA-1, BxPC3 and PANC-1) were incubated with increasing concentrations (1, 10, 20, 50, and 100 nm) of either free paclitaxel (black bar) or equivalent amount of nanopaclitaxel (grey bar) for 48 hours. Also included as control in each condition were void polymeric nanoparticle equal to the amount required for encapsulating said dose of nanopaclitaxel (white bar) and solvent (dimethylsulfoxide [DMSO], blue bar) equal to the amount required for dissolving said dose of free paclitaxel. Nanopaclitaxel (grey bar) demonstrates comparable cytotoxicity in all three cell lines in vitro, compared to free paclitaxel (black bar). Thus, nano-encapsulation of the drug is not associated with loss of drug activity. In contrast, and as expected, treatment with the void polymer only does not demonstrate any significant effect of cytotoxicity compared to baseline control growth of the cells (0 nm condition). All assays were performed in triplicate and error bars represent standard deviations.
Figure 6B:
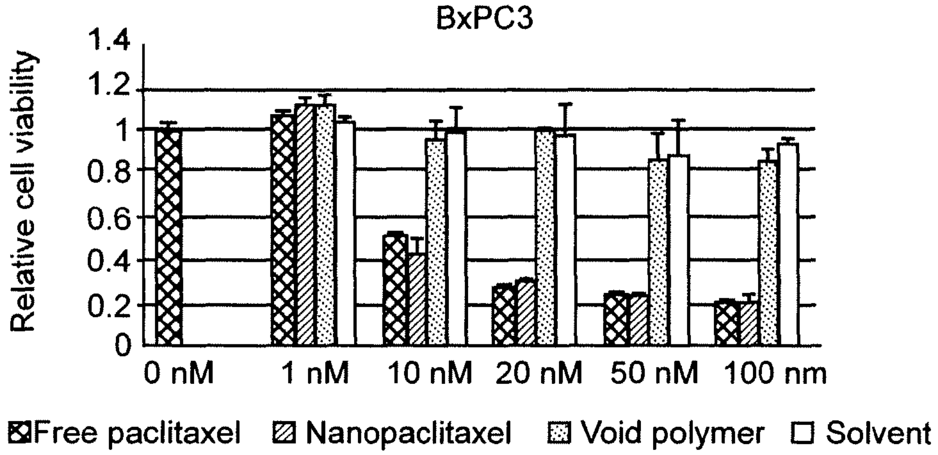
Figure 6C:
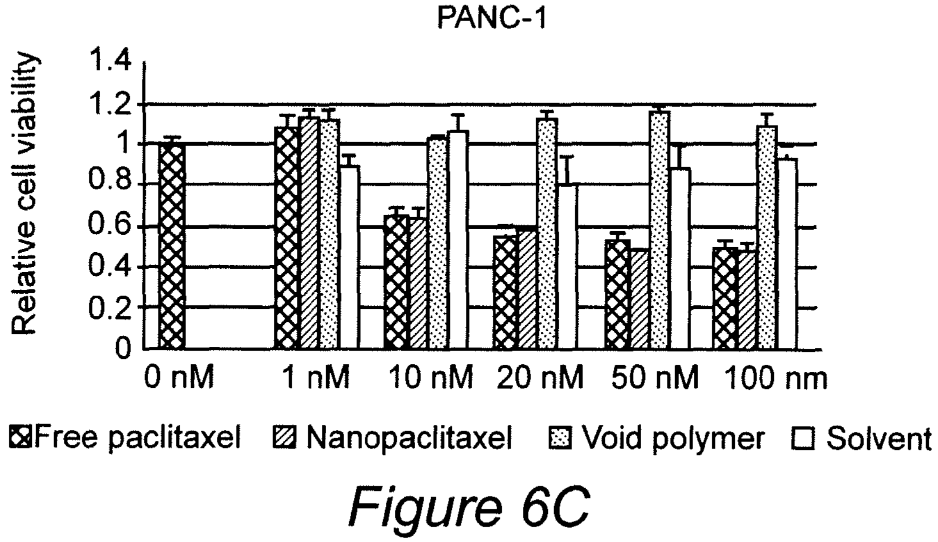
Figure 8:
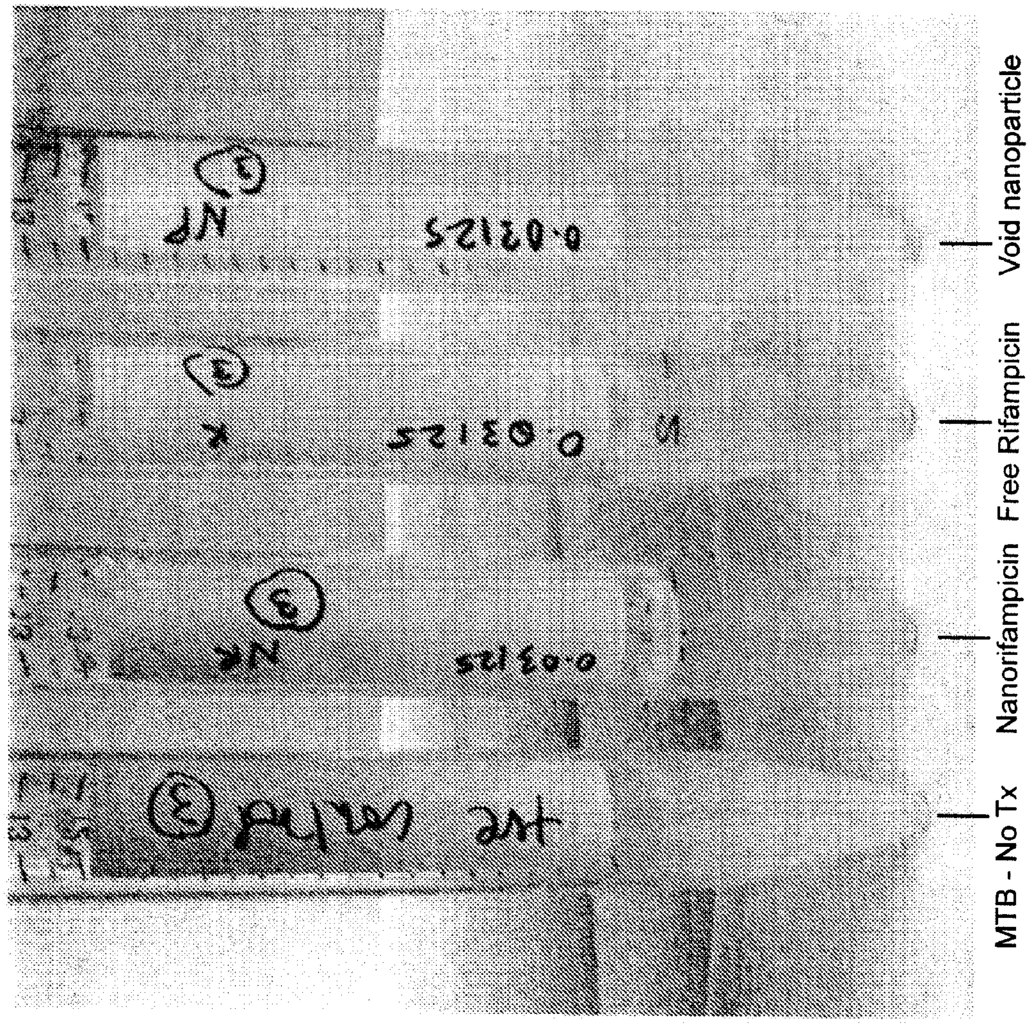
FIG. 8 illustrates the bactericidal effects of nanoparticle encapsulated rifampicin and free rifampicin against *Mycobacterium tuberculosis* (MTB). In this experiment, MTB was cultured for two weeks in absence of any treatment, nano-encapsulated rifampicin, free rifampicin, and void nanoparticles. There is robust MTB growth in the no treatment and in the void nanoparticle tubes, the latter consistent with lack of toxicity from the polymer per se. In contrast, MTB growth is completely inhibited in the nano-encapsulated rifampicin and free rifampicin tubes.

In Vitro Growth Assays of Nanoparticle Formulation of an Anticancer Agent, and an Example of Combination Therapy Achieved Using Nanoparticle Formulations of Two Independent Anticancer Agents Paclitaxel is a poorly water soluble anticancer agent, and can be solubilized for dispersion in aqueous media using the polymeric nanoparticles described herein. Nanopaclitaxel encapsulated in NVA631 particles were utilized for in vitro cell viability (MTT) assays in a panel of three human pancreatic cancer cell lines (XPA-1, BxPC3, and PANC-1). The results of this study are presented in FIG. 6. As seen, the nanopaclitaxel demonstrates comparable potency to free drug for any given dose of paclitaxel, confirming that the process of nano-encapsulation does not diminish the activity of parent compound. The results of two independent therapeutic agents (nanopaclitaxel and nanocurcumin) are presented in FIG. 7. As seen, the combination of nanopaclitaxel and nanocurcumin demonstrates increased cytotoxicity than either free paclitaxel or nanopaclitaxel alone at any given dose of paclitaxel. Of note, and especially at the lower dosages used in two of the cell lines (XPA-1 and Panc-1), the combination of nanopaclitaxel and nanocurcumin also appears to have better efficacy than the combination of free paclitaxel and free curcumin, likely due to increased intracellular uptake of the nano-encapsulated compounds. At higher dosages, the combination therapy with either free or nano-encapsulated drugs appears to have comparable effects.

Example 7

Surface Modification of Polymeric Nanoparticle Formulation by a Taste Masking Agent Aspartame, and Encapsulation of the Antifungal Agent Griseofulvin in the Surface Modified Nanoparticles The antifungal agent griseofulvin is poorly water soluble, has poor oral bioavailability, and has a bitter taste that can affect patient compliance. In this example, we demonstrate the utility of "smart" polymeric nanoparticles (illustrative example is the composition NMA622) in being amenable to surface modification by taste masking agents, and the incorporation of griseofulvin within such modified nanoparticles. 10 ml of NMA 622 polymer nanoparticles dispersion (containing 100 mg of polymer) was mixed with 500 μl of 5 mM EDCI by stirring for complete dissolution. To the clear dispersion, 30 mg of solid Aspartame was added. The solution was stirred over night for 15 to 20 hours. The clear solution was then dialyzed through 12 kD cut off dialysis bag for 4 hours with change of external water at every one hour. To the dialyzed solution, 2 mg of solid griseofulvin was added, and the solution was sonicated for 30 mins for complete dispersion, followed by gentle heating with stirring at 50 to 60 C to achieve a clear solution. If required, the process of sonication followed by gentle heating with stirring was repeated till the solution was clear. The clear solution of nano-griseofulvin at room temperature was lyophilized to a dry powder for further use.

The release kinetics of griseofulvin from surface aspartame-conjugated polymeric nanoparticles at room temperature was further studied. 10 mg of lyophilized powder of griseofulvin loaded, surface modified NMA622 polymeric nanoparticles (designated "nano-griseofulvin") were dissolved in 1 ml of water by vortexing. Then, 10 μl of the clear solution of nano-griseofulvin was added to 1 ml of water and the absorbance of the mixture was taken at 292 nm. After every two hours, the original nano-griseofulvin solution was centrifuged at 2000 rpm for 10 mins, and 10 μl of the centrifugate was pipetted carefully from the surface and was added to 1 ml of water. Absorbance was taken at 292 nm. After 10 hours, the original nano-griseofulvin solution was kept over night, and the 292 nm absorbance at 24 hours was measured, as described above. The absorbance was similarly measured at 48 and 72 hours. The % of release was calculated from the equation (Do−Dt)/Do×100 where Do is the absorbance at zero hours and Dt is the absorbance at t hours. In this calculation it is assumed that practically all the griseofulvin released from the nanoparticles settles down during centrifugation and that the concentration of griseofulvin in water is practically zero.

Results:

| Time | OD | % release |
|---|---|---|
| 0 hr | 0.093 | 0.0 |
| 2 hrs | 0.085 | 8.6 |
| 4 hrs | 0.076 | 18.3 |
| 6 hrs | 0.072 | 23.0 |
| 10 hrs | 0.061 | 34.4 |
| 24 hrs | 0.053 | 43.0 |
| 48 hrs | 0.048 | 48.4 |
| 72 hrs | 0.018 | 80.6 |

This example demonstrates the encapsulation of another poorly water soluble drug, the antifungal agent griseofulvin, in the said polymeric nanoparticles, and the ability to alter the innate taste of the encapsulated medicament by taste masking agents conjugated to the nanoparticle surface. This example also demonstrates the favorable release kinetics of the nanoparticle-loaded drug over 72 hours, including absence of any "burst release" effects.

Example 8

Figure 9:
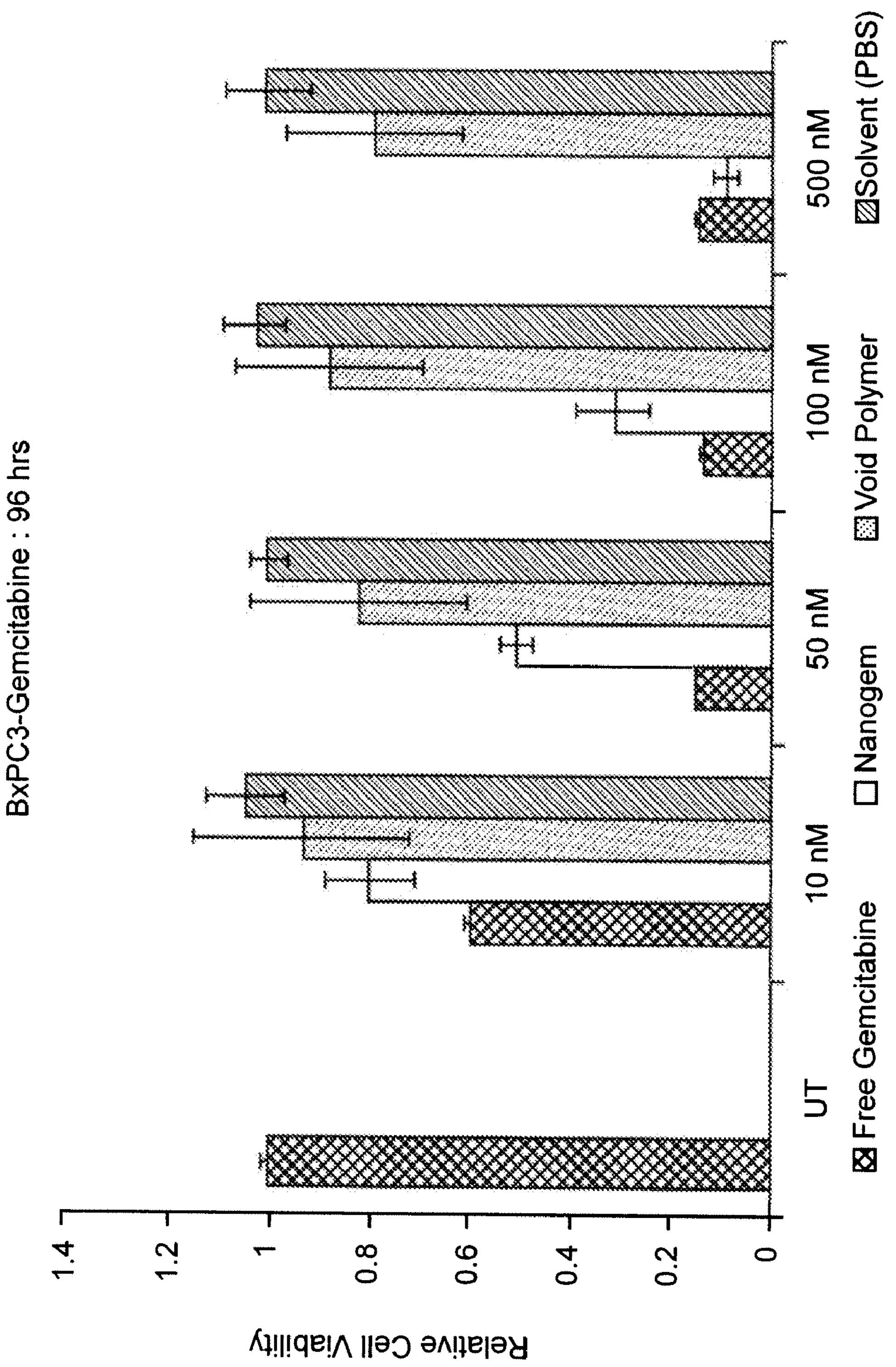
FIG. 9 illustrates in vitro cell viability (MTT assay) performed using the water-soluble drug gemcitabine conjugated to the acrylic acid (AA) surface reactive functional group of polymeric nanoparticle. Unlike the poorly water drugs that are encapsulated within the nanoparticle, water soluble drugs like gemcitabine can be conjugated to the nanoparticle surface, rendering this compound amenable to oral delivery. Human pancreatic cancer cell line BxPC3 is incubated with increasing dosages of either free gemcitabine (black bar), nano-gemcitabine (white bar), void polymer (grey bar), or PBS solvent (patterned bar). UT=untreated. At 96 hours, free gemcitabine and nano-gemcitabine demonstrated comparable activity. All assays were performed in triplicate and means and standard deviations are plotted.

Conjugation of Water Soluble Anticancer Drug Gemcitabine on the Surface of Polymeric Nanoparticles and the Application of Said "Nano-Gemcitabine" Preparation to In Vitro Cell Viability Assays in Human Cancer Cell Lines Gemcitabine is a water soluble compound, and thus differs from the poorly water soluble drugs discussed above that are encapsulated within the hydrophobic core of the polymeric nanoparticles. Herein, we describe the chemical conjugation of gemcitabine, as one illustrative example of water soluble drugs, to the hydrophilic surface of the polymeric nanoparticles. Such conjugation is expected to render gemcitabine amenable to oral delivery, utilizing the oral bioavailability properties of the said polymeric nanoparticles used as a carrier. 10 mg of NMA622 polymeric nanoparticles were dispersed in 10 ml of water by vortexing. To the clear solution, 6.5 mg of EDCI was added and was stirred for 10 mins. Thereafter, 10.2 mg of gemcitabine powder was added, while stirring was continued. The solution was stirred further for 15-20 hours. The clear solution was then dialysed for 3 hours through 12 kD dialysis membrane against water. It was then lyophilized to dry powder for further use. In order to demonstrate retained anti-cancer effects of gemcitabine conjugated to polymeric nanoparticles, cell viability (MTT) assays were done as described in example 6, using the human pancreatic cancer cell line BxPC3. FIG. 9 confirms that nano-gemcitabine has comparable potency to free gemcitabine at 96 hours.

While the invention has been described in terms of its preferred embodiments, those skilled in the art will recognize that the invention can be practiced with modification within the spirit and scope of the appended claims.

What is claimed is:

1. A method for preparing polymeric nanoparticles having a lower critical solution temperature (LCST) above 37° C., comprising the steps of:

dissolving in aqueous fluid to form micelles from monomers consisting of

N-isopropylacrylamide (NIPAAM), acrylic acid (AA), and at least one vinyl monomer selected from the group consisting of vinyl acetate, 4-vinyl benzoic acid, methylmethacrylate, vinylmethacrylate, N-vinylpyrrolidone, N-vinyl piperidone, N-vinyl caprolactum, N-vinyl carbazole, and styrene, wherein said NIPAAM, said AA, and said vinyl monomer are present at molar ratios of 50-70:10-30:10-30 for NIPAAM:AA:vinyl monomer;

polymerizing said micelles;

removing unreacted materials from said solution;

adding one or more bioactive agents to said solution and allowing said one or more bioactive agents to become entrapped within polymerized micelles in said solution or to become conjugated to the surface of said polymerized micelles in said solution, and functionalizing AA with polyethylene glycol (PEG) amine.

2. The method of claim 1 wherein said polymerizing step includes the step of adding one or more of a crosslinking agent, an activator, and an initiator.

3. The method of claim 1 wherein said polymerizing step is performed in the presence of an inert gas.

4. The method of claim 1 wherein said polymerizing step is performed at a temperature ranging from 20° C. to 80° C.

5. The method of claim 4 wherein said temperature ranges from 30° C. to 40° C.

6. The method of claim 1 wherein said polymeric nanoparticles have a diameter of 50-100 nm or smaller.

7. The method of claim 1 wherein at least one of said one or more bioactive agents becomes entrapped within said micelles.

8. The method of claim 1 wherein at least one of said one or more bioactive agents is a medicament.

9. The method of claim 1 wherein at least one of said bioactive agents is selected from the group consisting of antineoplastic agents, steroidal compounds, flavonoids, curcuminoids, phytochemicals, antifungal agents, antiviral agents, antibacterial agents, antitubercular agents, and anti-inflammatory agents.

10. The method of claim 1 wherein at least one of said one or more bioactive agents is selected from the group consisting of Paclitaxel, Docetaxel, Rapamycin, Doxorubicin, Daunorubicin, Idarubicin, Epirubicin, Capecitabine, Mitomycin C, Amsacrine, Busulfan, Tretinoin, Etoposide, Chlorambucil, Chlormethine, Melphalan, Gemcitabine, 5-fluorouracil, (5-FU), Benzylphenylurea (BPU) compounds, Curcumin, Curcuminoids, Cyclopamine, Aciclovir, Indinavir, Lamivudine, Stavudine, Nevirapine, Ritonavir, Ganciclovir, Saquinavir, Lopinavir, Nelfinavir, Itraconazole, Ketoconazole, Miconazole, Oxiconazole, Sertaconazole, Amphotericin B, Griseofulvin Ciprofloxacin, Moxifloxacin, Ofloxacin, Methoxyfloxacin, Pefloxacin, Norfloxacin, Sparfloxacin, Temafloxacin, Levofloxacin, Lomefloxacin, Cinoxacin, Cloxacillin, Benzylpenicillin, Phenylmethoxypenicillin, Erythromycin, Rifampicin, Rifapentin, Ibuprofen, Indomethacin, Ketoprofen, Naproxen, Oxaprozin, Piroxicam, and Sulindac.

11. The method of claim 1 further comprising the step of surface modification of the particles by functionalizing AA in said polymerized micelles after, said polymerizing step with polyethylene glycol (PEG) amine.

12. The method of claim 11 wherein a functionalizing step is performed by chemical conjugation between surface carboxylic groups of AA on said polymerized micelles and terminal amine groups of PEG or derivatives of PEG using a cross linker.

13. The method of claim 1 further comprising the step of surface modification of particles by chemically conjugating the carboxylic groups of the said polymeric micelle with the amine group of a conjugated moiety.

14. The method of claim 13 wherein said conjugated moiety is selected from the group consisting of a contrasting agent, an antibody, a ligand to a cell surface receptor, a fluorophore, a dye, a radionuclide, a water soluble medicament, and a taste masking agent.

15. A process for preparing polymeric nanoparticles compositions, comprising the steps of incorporating one or more medicament or bioactive agent into a polymeric nanoparticle consisting of monomers selected from NIPAAM at a molar ratio ranging from 50 to 70, acrylic acid (AA) at a molar ratio ranging from 10 to 30, and at least one vinyl monomer selected from the group consisting of vinyl acetate, 4-vinyl benzoic acid, methylmethacrylate, vinylmethacrylate, N-vinylpyrrolidone, N-vinyl piperidone, N-vinyl caprolactum, N-vinyl carbazole, and styrene, at a molar ratio ranging from 10 to 30 such that said one or medicament or bioactive agent is incorporated into said polymeric nanoparticle and said polymeric nanoparticle includes NIPAAM, AA, and at least one vinyl monomer present at molar ratios of 50-70:10-30:10-30 for NIPAAM:AA:vinyl monomer; and recovering polymeric nanoparticles after said incorporating step and functionalizing AA with polyethylene glycol (PEG) amine.

16. The method of claim 1 wherein said one or more bioactive agents added in said adding step includes curcumin.

17. The method of claim 15 wherein said one or more medicament or bioactive agent includes curcumin.

* * * * *